United States Patent
Al-Ghamdi

(10) Patent No.: US 12,312,945 B1
(45) Date of Patent: May 27, 2025

(54) SYSTEM AND METHOD FOR WELLBORE IDENTIFICATION IN MULTI-LATERAL WELLBORES

(71) Applicant: SAUDI ARABIAN OIL COMPANY, Dhahran (SA)

(72) Inventor: Ahmed Abdullah Al-Ghamdi, Al Khobar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 18/400,827

(22) Filed: Dec. 29, 2023

(51) Int. Cl.
*E21B 47/09* (2012.01)
*E21B 41/00* (2006.01)
*G01N 31/22* (2006.01)
*G01N 33/28* (2006.01)

(52) U.S. Cl.
CPC .......... *E21B 47/09* (2013.01); *E21B 41/0035* (2013.01); *G01N 31/22* (2013.01); *G01N 33/2823* (2013.01)

(58) Field of Classification Search
CPC ..... E21B 47/09; E21B 41/0035; G01N 31/22; G01N 33/2823
See application file for complete search history.

(56) References Cited

U.S. PATENT DOCUMENTS

| | | | |
|---|---|---|---|
| 10,858,931 B2 | 12/2020 | Chen et al. | |
| 2011/0240287 A1* | 10/2011 | Hartshorne | E21B 47/11 166/250.12 |
| 2016/0024904 A1 | 1/2016 | Zupanick | |
| 2017/0260834 A1 | 9/2017 | Chacon et al. | |
| 2019/0055839 A1* | 2/2019 | Skillingstad | E21B 33/12 |
| 2019/0100973 A1* | 4/2019 | Lauritzen | E21B 23/01 |

FOREIGN PATENT DOCUMENTS

| | | | |
|---|---|---|---|
| CA | 2436173 A1 | | 1/2004 |
| NO | 20211590 A1 | * | 12/2021 |
| WO | 2021072447 A1 | | 4/2021 |

* cited by examiner

*Primary Examiner* — D. Andrews
*Assistant Examiner* — Ronald R Runyan
(74) *Attorney, Agent, or Firm* — Vorys, Sater, Seymour and Pease, LLP

(57) ABSTRACT

A well system includes a service rig positioned above a wellbore including a primary wellbore and a lateral wellbore extending from the primary wellbore, a string of casing lining a portion of the primary wellbore and having an inner surface coated with a first reactive material, a liner lining a portion of the lateral wellbore and having an inner surface coated with a second reactive material, a downhole tool conveyable into the wellbore to discharge a corrosive fluid reactable with the reactive materials and generate a reacted solution including a reaction product indicative of the first or second reactive material, and a fluid analyzer to analyze the reacted solution and identify the reaction product entrained in the reacted solution, wherein identifying the reaction product with the fluid analyzer provides a positive indication of a location of the downhole tool within the wellbore.

20 Claims, 2 Drawing Sheets

SYSTEM AND METHOD FOR WELLBORE IDENTIFICATION IN MULTI-LATERAL WELLBORES

FIELD OF THE DISCLOSURE

The present disclosure relates generally to multilateral wellbores and, more particularly, to positively identifying entrance into particular lateral wellbores in cased or lined multilateral wellbores.

BACKGROUND OF THE DISCLOSURE

With the continued development of hydrocarbon exploration, drilling and production techniques in areas that often comprise complex geology, multilateral wellbores have become prominent solutions. A multilateral wellbore consists of a main or "primary" wellbore and one or more deviated or "lateral" wellbores (or legs) extending from the primary wellbore. Multilateral wellbores allow for production from multiple reservoirs and are generally more cost effective in both well construction and reservoir management.

During well intervention activities, coiled tubing is lowered into the different lateral wellbores to undertake a variety of stimulation operations, such as pumping acid and stimulate the laterals to enhance production rates. The coiled tubing is able to navigate between the lateral boreholes using a multi-lateral tool (MLT). However, even with the MLT, accurately locating and entering a desired lateral leg can be problematic as proper identification of specific lateral wellbores within a multilateral wellbore can be difficult. While the different laterals have different maximum depths, it is rare that coiled tubing is able to reach the end of each lateral to confirm the lateral from the final tag depth. Instead, well operators commonly rely on pressure signals, which are often difficult to interpret. As a result, accurate re-entry into lateral wellbores by means of coiled tubing can be particularly challenging.

The systems and methods disclosed herein provide an effective solution to said re-entry challenges.

SUMMARY OF THE DISCLOSURE

Various details of the present disclosure are hereinafter summarized to provide a basic understanding. This summary is not an exhaustive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

According to an embodiment consistent with the present disclosure, a well system, may include a service rig positioned above a wellbore penetrating a subterranean formation, wherein the wellbore may include a primary wellbore and a lateral wellbore extending from the primary wellbore. A string of casing may line at least a portion of the primary wellbore and may have an inner surface coated with a first reactive material. A liner may line at least a portion of the lateral wellbore and may have an inner surface coated with a second reactive material different from the first reactive material. The well system may further include a downhole tool conveyable into the wellbore from the service rig, wherein the downhole tool may be operable to discharge a corrosive fluid reactable with the first or second reactive material and may generate a reacted solution that includes a reaction product indicative of the first or second reactive material. The well system may also include a fluid analyzer arranged at the service rig that may be operable to analyze the reacted solution and identify the reaction product entrained in the reacted solution, wherein identifying the reaction product with the fluid analyzer may provide a positive indication of a location of the downhole tool within the wellbore.

According to an embodiment consistent with the present disclosure, a method may include conveying a downhole tool from a service rig and into a wellbore penetrating a subterranean formation, wherein the wellbore may include a primary wellbore extending from the service rig and lined with casing having a portion of an inner surface of the casing coated with a first reactive material. The wellbore may also include a lateral wellbore extending from the primary wellbore and lined with a liner having a portion of an inner surface of the liner coated with a second reactive material different from the first reactive material. The method may also include pumping a corrosive fluid to the downhole tool and discharging the corrosive fluid into the wellbore from the downhole tool and reacting the corrosive fluid with one of the first and second reactive materials and thereby generating a reacted solution including a reaction product indicative of the one of the first and second reactive materials. The method may also include circulating the reacted solution and the reaction product to the service rig, as well as analyzing the reacted solution at the service rig with a fluid analyzer and thereby identifying the reaction product. Lastly, the method may conclude by determining a location of the downhole tool within the wellbore based on identification of the reaction product.

According to an embodiment consistent with the present disclosure, a method may include conveying a downhole tool from a service rig and into a wellbore penetrating a subterranean formation, wherein the wellbore may include a primary wellbore extending from the service rig, and a first lateral wellbore extending from the primary wellbore and lined with a first liner having a portion of an inner surface of the first liner coated with a first reactive material. The wellbore may further include a second lateral wellbore extending from the primary wellbore and lined with a second liner having a portion of an inner surface of the second liner coated with a second reactive material different from the first reactive material. The method may include pumping a corrosive fluid to the downhole tool and discharging the corrosive fluid into the wellbore from the downhole tool and reacting the corrosive fluid with one of the first and second reactive materials and thereby generating a reacted solution including a reaction product indicative of the one of the first and second reactive materials. The method may also include circulating the reacted solution and the reaction product to the service rig, analyzing the reacted solution at the service rig with a fluid analyzer and thereby identifying the reaction product, and determining a location of the downhole tool within the first or second lateral wellbores based on identification of the reaction product.

Any combinations of the various embodiments and implementations disclosed herein can be used in a further embodiment, consistent with the disclosure. These and other aspects and features can be appreciated from the following description of certain embodiments presented herein in accordance with the disclosure and the accompanying drawings and claims.

DETAILED DESCRIPTION

Figure 1:
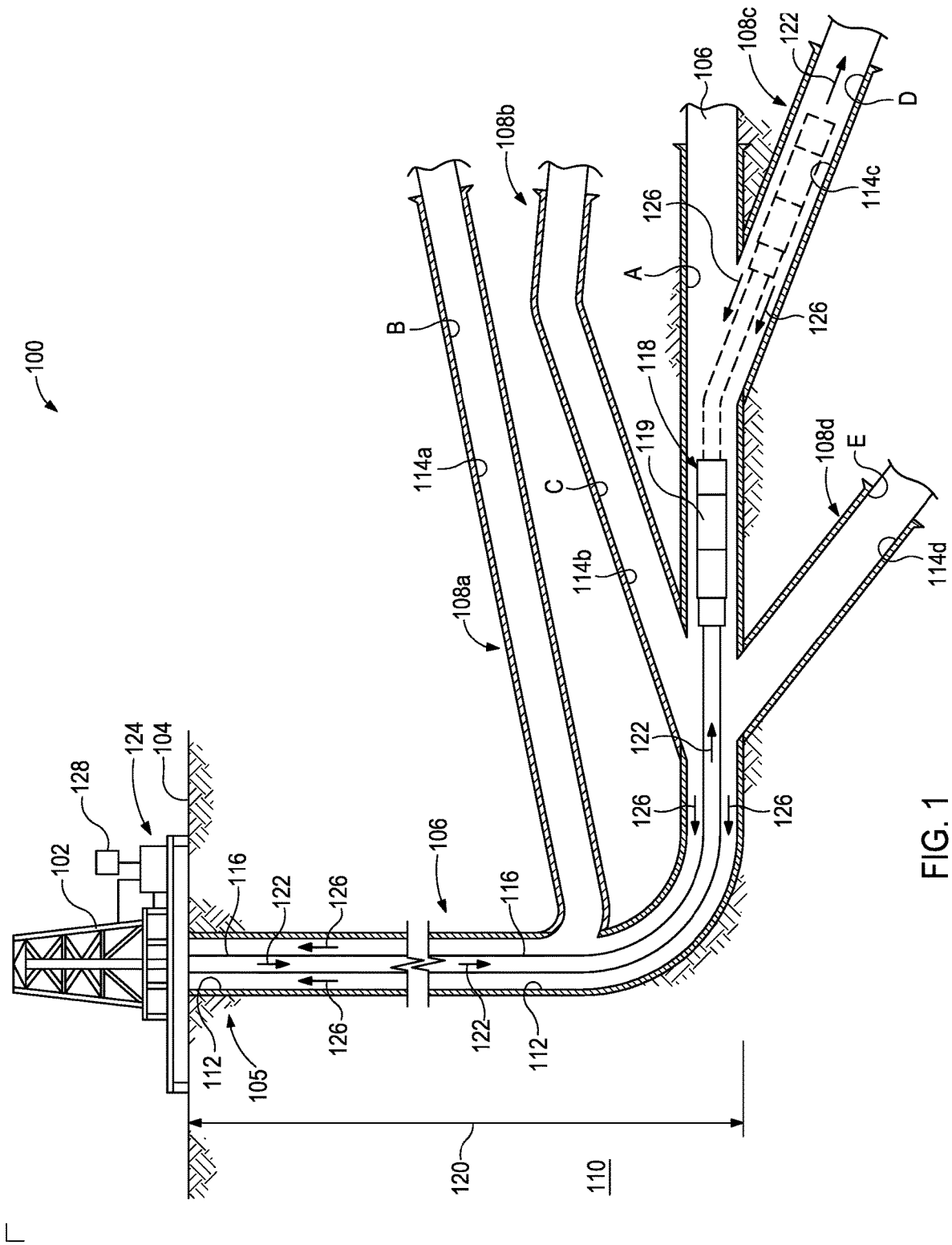
FIG. 1 is a schematic diagram of an example multilateral wellbore system that may employ one or more principles of the present disclosure.

Embodiments of the present disclosure will now be described in detail with reference to the accompanying Figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

Embodiments in accordance with the present disclosure generally relate to multilateral wellbores and, more particularly, to accurately reentering specific lateral wellbores of a multilateral wellbore with coiled tubing for the purpose of performing stimulation operations. A multilateral wellbore may have one or more lateral wellbores or "legs" extending from a main or "primary" wellbore. Once drilled and completed, either prior to or after initial production, each lateral wellbore may require a discrete stimulation treatment specific to the needs and/or requirements of the lateral wellbore and/or the formation in which the lateral was drilled. Re-entry into the lateral wellbore to perform said stimulation treatments is often accomplished using a multi-lateral tool (MLT) coupled to an end of coiled tubing. Because each lateral may require a specific or specialized treatment, knowledge of which lateral the coiled tubing has entered is critical. Inadvertent entry into the wrong lateral wellbore can result in the application of an incompatible treatment and/or unnecessary data acquisition runs, both of which are costly. Additionally, application of an improper stimulation treatment can be highly detrimental to the performance of the wellbore overall. Such an occurrence can result in a loss of hydrocarbon production and an undesirable increase in water production. The systems and methods disclosed herein provide a well operator with confirmation and a positive indicator as to which lateral wellbore has been entered. As a result, potential time and cost savings may be realized.

FIG. 1 is a schematic diagram of an example multilateral well system 100, (hereinafter referred to as the "system 100") that may employ one or more principles of the present disclosure. The system 100 may include a service rig 102 positioned on a terranean surface 104. The service rig 102 may include but is not limited to a drilling rig, a completion rig, a workover rig, a wellhead, or any combination thereof. Similarly, it will be appreciated by those skilled in the art that the various embodiments discussed herein are equally well suited for use in conjunction with other types of oil and gas platforms or rigs, such as offshore positioned oil and gas rigs or rigs located at any other geographical site. In the alternative, the embodiments and operations disclosed herein may be carried out without use of a service rig 102 and instead conducted with the well-intervention equipment deemed necessary by the well operator (rigless operations).

A wellbore 105 extends below the service rig 102 and into a subsurface (subterranean) formation 110. As depicted, the wellbore 105 includes a main or "primary" wellbore 106 extending from the service rig 102, and one or more lateral wellbores (alternately referred to as "legs" or "secondary wellbores") shown as lateral wellbores 108a, 108b, 108c and 108d that extend from the primary wellbore 106. It will be appreciated by those skilled in the art that even though FIG. 1 depicts four lateral wellbores 108a-d, the system 100 may comprise more or less than four lateral wellbores 108a-d without departing from the scope of the disclosure. Similarly, while the primary wellbore 106 is depicted as extending vertically and then transitioning in a generally horizontal direction, the embodiments described herein are equally applicable to a primary wellbore that may be entirely vertical or deviated. Similarly, the lateral wellbores 108a-d may comprise any deviation or direction without exceeding the scope of the system and methods disclosed herein.

As shown in FIG. 1, the primary wellbore 106 is lined with a string of casing 112 extending from the surface 104 and into the subsurface formation 110. Similarly, each lateral wellbore 108a-d is lined with a corresponding liner 114a-d operatively coupled to and extending from the casing 112. In other embodiments, the primary wellbore 106 and the lateral wellbores 108a-d may be lined with any configuration of casing, liners, and/or tubing strings that may be operationally desirable and/or necessary. Accordingly, the construction and tubular configuration of each of the respective wellbores 106, 108a-d may be at the discretion of the well operator and is therefore not limiting to this disclosure.

After the system 100 is put onto production and the primary wellbore 106 and/or any combination of the lateral wellbores 108a-d begin to produce hydrocarbons, over time, production may begin to lessen or taper off. In such instances, the well operator may find it necessary to re-enter the primary wellbore 106 and any or all of the connected lateral wellbores 108a-d to perform stimulation treatments designed to improve (enhance) hydrocarbon production. In some applications, this can be done by deploying an extension of coiled tubing 116 for the purposes of re-entry into any or all of the wellbores 106, 108a-d.

As illustrated, the coiled tubing 116 extends from the service rig 102 and into the primary wellbore 106. The coiled tubing 116 may be run in hole and extend into any of the lateral wellbores 108a-d, and may be able to advance into all lateral wellbores 108a-d in a single downhole run (trip). A downhole tool 118 may be operatively and fluidly coupled to the distal end of the coiled tubing 116. In at least one embodiment, the downhole tool 118 may include a steering tool 119 operable to help guide or direct the coiled tubing 116. In such embodiments, the steering tool 119 may include a multi-lateral tool (MLT) that is selectively operable to change the trajectory of the coiled tubing 116 and thereby allow the coiled tubing 116 to enter any of the lateral wellbores 108a-d. Once positioned within a given lateral wellbore 108a-d, the downhole tool 118 may further include one or more components, tools, or devices operable to execute (undertake) a stimulation treatment specific to the given lateral wellbore 108a-d.

Because each of the lateral wellbores 108a-d may be targeting different and specific zones within the formation 110, and each zone may exhibit varying geological properties, it may be necessary to execute wellbore-specific stimulation treatments in each of the wellbores 106, 108a-d. For this reason, it is critical to confirm which lateral wellbore 108a-d the downhole tool 118 has entered for the purposes of executing a compatible stimulation treatment. By way of example, the downhole tool 118 may be extended into the primary wellbore 106 for the purpose of re-entering the third lateral wellbore 108c. In conventional operations, confirmation of re-entry into the third lateral wellbore 108c may be accomplished by advancing the downhole tool 118 to the known final depth of the third lateral wellbore 108c. In particular, when drilling the respective lateral wellbores 108a-d, the well operator will have acquired surveys including location information at associated depths, for each of the respective wellbores 106, 108a-d. As a result, the well operator will have knowledge of the discrete final depth for each respective wellbore 106, 108a-d prior to performing any stimulation treatment.

Upon reentering and successfully reaching the final depth of the third lateral wellbore 108c with the downhole tool 118, doing so may provide confirmation that the "correct" lateral wellbore 108c has been entered. However, over time and during production, the wellbores 106, 108a-d often experience buildup of debris or other fill (e.g., material and/or sediment fallen out from drilling fluids, formation fluids, production fluids, etc.) that makes reaching final depth on re-entry unlikely and often impossible. In such instances, the well operator is not able to acquire definitive confirmation that the third lateral wellbore 108c has actually been reentered. Furthermore, a depth-confirmed method of re-entry is time consuming wherein one or more incorrect lateral wellbores 108a-d may be re-entered before eventually confirming re-entry into the intended third lateral wellbore 108c. For this reason, other conventional methods of confirming re-entry are sometimes utilized, such as relying upon the observance and identification of variances in pump pressure. However, these methods may too prove problematic especially if consistent and required pump rates and pressures are not maintained.

According to embodiments of the present disclosure, re-entry into any of the lateral wellbores 108a-d may be confirmed with greater certainty with the methods disclosed herein. Prior to deploying the liners 114a-d downhole and installing them within their respective lateral wellbores 108a-d, a portion of the inner surface of each liner 114a-d may be coated with a chemical composition unique to each liner 114a-d and comprising a reactive material capable of reacting with (reactable with) a corrosive fluid. Consequently, once installed, the corresponding liner 114a-d and more particularly, the corresponding lateral wellbore 108a-d may be identified upon re-entry with the downhole tool 118. In some embodiments, a portion of the inner surface of the casing 112 may also be coated with a unique chemical composition capable of reacting with a corrosive fluid to help determine when the downhole tool 118 is present within the primary wellbore 106.

In FIG. 1, a portion of the inner surface of the casing 112 may be coated with a first reactive material "A", a portion of the inner surface of the first liner 114a may be coated with a second reactive material "B", a portion of the inner surface of the second liner 114b may be coated with a third reactive material "C", a portion of the inner surface of the third liner 114c may be coated with a fourth reactive material "D", and a portion of the inner surface of the fourth liner 114d may be coated with a fifth reactive material "E". The reactive materials A-E may each be different (unique) and may comprise a chemical compound that is dissolvable in the presence of a particular solution or chemical, referred to herein as a "corrosive fluid". The reactive materials A-E may include, but are not limited to, calcium carbonate ($CaCO_3$), zinc (Zn), aluminum (Al), manganese (Mn), nickel (Ni), copper (Cu), and barium (Ba). Other reactive materials may be desirable and the aforementioned example reactive materials should not be considered to be limiting to the scope of this disclosure.

Each of the reactive materials A-E may be compatible with the existing formation fluids to prevent consumption or deterioration of the coating prior to well intervention. In some embodiments, each of the reactive materials A-E may be dissolvable in the presence of the corrosive fluid, which may comprise, for example, hydrochloric acid (HCl). Examples of other corrosive fluids that may be used include, but are not limited to, sulfuric acid ($H_2SO_4$), nitric acid ($HNO_3$), acetic acid ($CH_3COOH$), phosphoric acid ($H_3PO_4$), formic acid (HCOOH), and/or citric acid ($C_6H_8O_7$). Accordingly, any corrosive fluid may be used if the corrosive fluid is able to react with the reactive materials A-E and generate an identifiable reaction product, as discussed below. In determining the appropriate corrosive fluid, and similarly, the appropriate reactive materials A-E, consideration may be given to characteristics of the system 100 so as not to induce any unwanted effects, such as tubular corrosion. Specific characteristics that may be considered include, but are not limited to, the drilling fluid used, the completion fluid used, the formation fluid present, and tubular composition. In some instances the consideration of the lithology of the formation 110 may be dispositive in determining both the reactive material A-E and the corrosive fluid that may be used.

The coating of the unique reactive materials A-E may be applied to all or only a select section (portion) of the corresponding downhole tubular (e.g., the casing 112 or the liners 114a-d). In some embodiments, for example, the first reactive material A may be applied to the inner surface of the casing 112 along the lower (downhole) half of the casing 112, or could alternatively be applied to the inner surface of the casing only at or near the distal end of the casing 112. Similarly, the reactive materials B-E may be applied to only a portion of the respective inner surfaces of the liners 114a-d. In at least one embodiment, the reactive materials B-E may be applied to the distal ends of the liners 114a-d, the distal ends of the liners 114a-d being the kickoff point where the lateral wellbores 108a-d begin to divert from the primary wellbore 106. In such an embodiment, the reactive materials B-E may be applied to a predetermined amount (or percentage) of the distal portion of the liners 114a-d. For example, in some embodiments, ~25% of the most distal portion of the liners 114a-d may be coated with the respective reactive material B-E. In other embodiments, the reactive materials B-E may be applied to the entirety of the inner surface of or in the alternative, along the lower (downhole) portion of the liner 114a-d.

In at least one embodiment, the coating of the reactive materials A-E may be applied to the respective inner surfaces on site and otherwise at the location of the service rig 102 prior to installing the tubulars downhole. In other embodiments, the coating of the reactive materials A-E may be applied at the respective inner surfaces at the point of origin (e.g., distribution location) of each tubular, or alternatively during manufacture of the tubular. Once the discrete coatings of the reactive materials A-E have been applied to the respective tubulars, the casing 112 and liners 114a-d may be installed in accordance with well operator procedures.

As in the example provided above, when it is desired to re-enter the third lateral wellbore 108c, the coiled tubing 116 may be deployed downhole with the downhole tool 118 operatively coupled thereto. Using depth tracking and the aforementioned surveys, including a true vertical depth (TVD) 120, the downhole tool 118 may be advanced to the approximate depth at which the third lateral wellbore 108c is known to be located. Upon reaching the desired TVD 120, the downhole tool 118 may be operated to guide the coiled tubing 116 into the third lateral wellbore 108c.

To provide positive indication that the downhole tool 118 has entered the third lateral wellbore 108c, a corrosive fluid 122 may be injected into the third lateral wellbore 108 from the downhole tool 118. More specifically, the system 100 may further include a fluid circulation system 124 arranged at or forming part of the service rig 102. The fluid circulation system 124 may be fluidly coupled to the coiled tubing 116 and include one or more pumps, fluid holding tanks, and associated plumbing operable to circulate fluids into the wellbore 106 and to the downhole tool 118 via the coiled tubing 116. At the downhole tool 118, the corrosive fluid 122 may be discharged into the surrounding downhole environment, such as through one or more nozzles or discharge ports (not shown) provided on the downhole tool 118 and in fluid communication with the coiled tubing 116. In at least one embodiment, at least five (5) barrels (bbls) of the corrosive fluid 122 may be circulated downhole and discharged into the surrounding downhole environment using the fluid circulation system 124.

Once discharged from the downhole tool 118, the corrosive fluid 122 will contact the interior body of the third liner 114c, which is coated with the fourth reactive material D. The corrosive fluid 122 will react with and dissolve some or all of the fourth reactive material D, thereby generating a reacted solution 126 comprising a fluid mixture of the corrosive fluid 122 and a reaction product resulting from the chemical reaction between the corrosive fluid 122 and the fourth reactive material D. For example, in embodiments where the fourth reactive material D is manganese (Mn) and the corrosive fluid 122 is hydrochloric acid (HCl), the resulting reaction product entrained within the reacted solution 126 would be manganese chloride ($MnCl_2$) and hydrogen ($H_2$) as generated by the following reaction: $Mn+2HCl \ acid \rightarrow MnCl_2+H_2$.

Continued pumping of the corrosive fluid 122 (or another fluid) will pump the reacted solution 126, including the reaction product, back to the service rig 102 within the annulus defined between the outer surface of the coiled tubing 116 and the inner walls of the wellbore 106. At the service rig 102, the system 100 may further include a fluid analyzer 128 arranged to receive and analyze the reacted solution 126 and, in particular, the reaction product entrained in the reacted solution 126. The fluid analyzer 128 may be operable to perform a variety of analyses. Examples of analyses the fluid analyzer 128 may be operable to perform includes, but is not limited to, mass spectrometry, x-ray fluorescence "XRF" spectroscopy, atomic absorption spectroscopy, fourier transform infrared spectroscopy (FTIR) ultraviolet-visible spectroscopy (UV-Vis), or any combination thereof.

Once the fluid analyzer 128 analyzes the reacted solution 126, a determination of the specific reaction product entrained in the reacted solution 126 may be obtained, thereby providing a positive indication of where the downhole tool 118 is located. For example, in the embodiment where the fourth reactive material D is manganese (Mn) and the corrosive fluid 122 is hydrochloric acid (HCl), if the fluid analyzer 128 determines that the reacted solution 126 includes manganese chloride ($MnCl_2$) as the reaction product, this may be a positive indication that the downhole tool 118 is located in the third lateral wellbore 108c where the fourth reactive material D was coated on the inner walls of the third liner 114c. In contrast, if the fluid analyzer 128 determines that the reacted solution 126 includes another reaction product not consistent with the fourth reactive material D, that may be an indication that the downhole tool 118 is not located in the third lateral wellbore 108c, but is instead located in one of the other lateral wellbores 108a,b,d, or possible in the primary wellbore 106.

In other embodiments, the operations disclosed herein may be conducted without a service rig 102 (rigless). In at least one rigless embodiment, a wellhead (not shown) may be arranged at the terranean surface 104 and operatively and fluidly coupled to the wellbore 106. The coiled tubing 116 and the downhole tool 118 may then be extended through the wellhead and into the wellbore 106 and/or the desired lateral wellbore(s) 114a-d. In the same manner described above to discern the location of the downhole tool 118, the corrosive fluid 122 may be pumped down the coiled tubing 116 for the purpose of reacting with the reactive materials A-E and thereby generating the reacted solution 126. The wellhead, more particularly, wellhead valves disposed within the wellhead, may be manipulated to allow the reacted solution 126 to flow naturally back to the wellhead. Once within the wellhead, the reacted solution 126 may flow from the wellhead and into a tank or flowline included within the fluid circulation system 124 and fluidly coupled to the wellhead. A sample of the reacted solution 126 may be collected from the tank or flowline and subsequently received into the fluid analyzer 128. In accordance with the same method described above, the fluid analyzer 128 may provide positive indication of the position of the downhole tool 118.

In embodiments where the first reactive material A is calcium carbonate ($CaCO_3$) and the corrosive fluid 122 is hydrochloric acid (HCl), the HCl will react with and dissolve some or all of the $CaCO_3$, thereby generating a reacted solution 126 with a reaction product of calcium chloride ($CaCl_2$)), carbon dioxide ($CO_2$), and water ($H_2O$) according to the following reaction: $CaCO_3+2HCl \rightarrow CaCl_2)+CO_2+H_2O$. If the first reactive material A is coated on the inner walls of the casing 112, and the fluid analyzer 128 determines that the reacted solution 126 includes $CaCl_2$) as the reaction product, this may be a positive indication that the downhole tool 118 is located in the primary wellbore 106.

In embodiments where the second reactive material B is zinc (Zn) and the corrosive fluid 122 is hydrochloric acid (HCl), the HCl will react with and dissolve some or all of the Zn, thereby generating a reacted solution 126 with a reaction product of zinc chloride ($ZnCl_2$) and hydrogen ($H_2$) according to the following reaction: $Zn+2HCl \rightarrow ZnCl_2+H_2$. If the second reactive material B is coated on the inner walls of the first liner 114a, and the fluid analyzer 128 determines that the reacted solution 126 includes $ZnCl_2$ as the reaction product, this may be a positive indication that the downhole tool 118 is located in the first lateral wellbore 108a.

In embodiments where the third reactive material C is aluminum (Al) and the corrosive fluid 122 is hydrochloric acid (HCl), the HCl will react with and dissolve some or all of the Al, thereby generating a reacted solution 126 with a reaction product of aluminum chloride ($AlCl_3$) and hydrogen ($H_2$) according to the following reaction: $2Al+6HCl \rightarrow 2AlCl_3+3H_2$. If the third reactive material C is coated on the inner walls of the second liner 114b, and the fluid analyzer 128 determines that the reacted solution 126 includes $AlCl_3$ as the reaction product, this may be a positive indication that the downhole tool 118 is located in the second lateral wellbore 108b.

In embodiments where the fifth reactive material E is nickel (Ni) and the corrosive fluid 122 is hydrochloric acid (HCl), the HCl will react with and dissolve some or all of the Ni, thereby generating a reacted solution 126 with a reaction product of nickel chloride ($NiCl_2$) and hydrogen ($H_2$) according to the following reaction: $Ni+2HCl\ acid \rightarrow NiCl_2 + H_2$. If the fifth reactive material E is coated on the inner walls of the fourth liner 114d, and the fluid analyzer 128 determines that the reacted solution 126 includes $NiCl_2$ as the reaction product, this may be a positive indication that the downhole tool 118 is located in the fourth lateral wellbore 108d.

Accordingly, if the well operator requires the downhole tool 118 to be located in the third lateral wellbore 108c, but the fluid analyzer 128 determines that the reacted solution 126 does not include a reaction product of $MnCl_2$, which is consistent with the fourth reactive material D, the well operator may retract the coiled tubing 116 in the uphole direction and attempt to reposition the downhole tool 118 within the third lateral wellbore 108c. Once the downhole tool 118 is advanced and purportedly within the third lateral wellbore 108c, the corrosive fluid 122 may again be pumped to the downhole tool 118 to react with the fourth reactive material D and generate the reacted solution 126, which is pumped back to the service rig 102 for analysis by the fluid analyzer 128. If the fluid analyzer 128 determines that the reacted solution 126 includes manganese chloride ($MnCl_2$) as the reaction product, this is a positive indication that the downhole tool 118 is successfully located in the third lateral wellbore 108c and a planned stimulation operation may then be undertaken in the third lateral wellbore 108c using the downhole tool 118.

The foregoing process may be repeated as needed in each lateral wellbore 108a-d and/or the primary wellbore 106 to provide positive indication of the current position of the downhole tool 118. Once a positive indication of the current location of the downhole tool 118 is determined, the planned stimulation operation for the particular lateral wellbore 108a-d and/or the primary wellbore 106 may then be undertaken using the downhole tool 118. Accordingly, the well operator may continue with any stimulation treatment (or otherwise) that may have been designed specifically for the lateral wellbores 108a-d or the primary wellbore 106, and similarly, for the formation 110 that the lateral wellbores 108a-d or the primary wellbore 106 penetrate.

Figure 2:
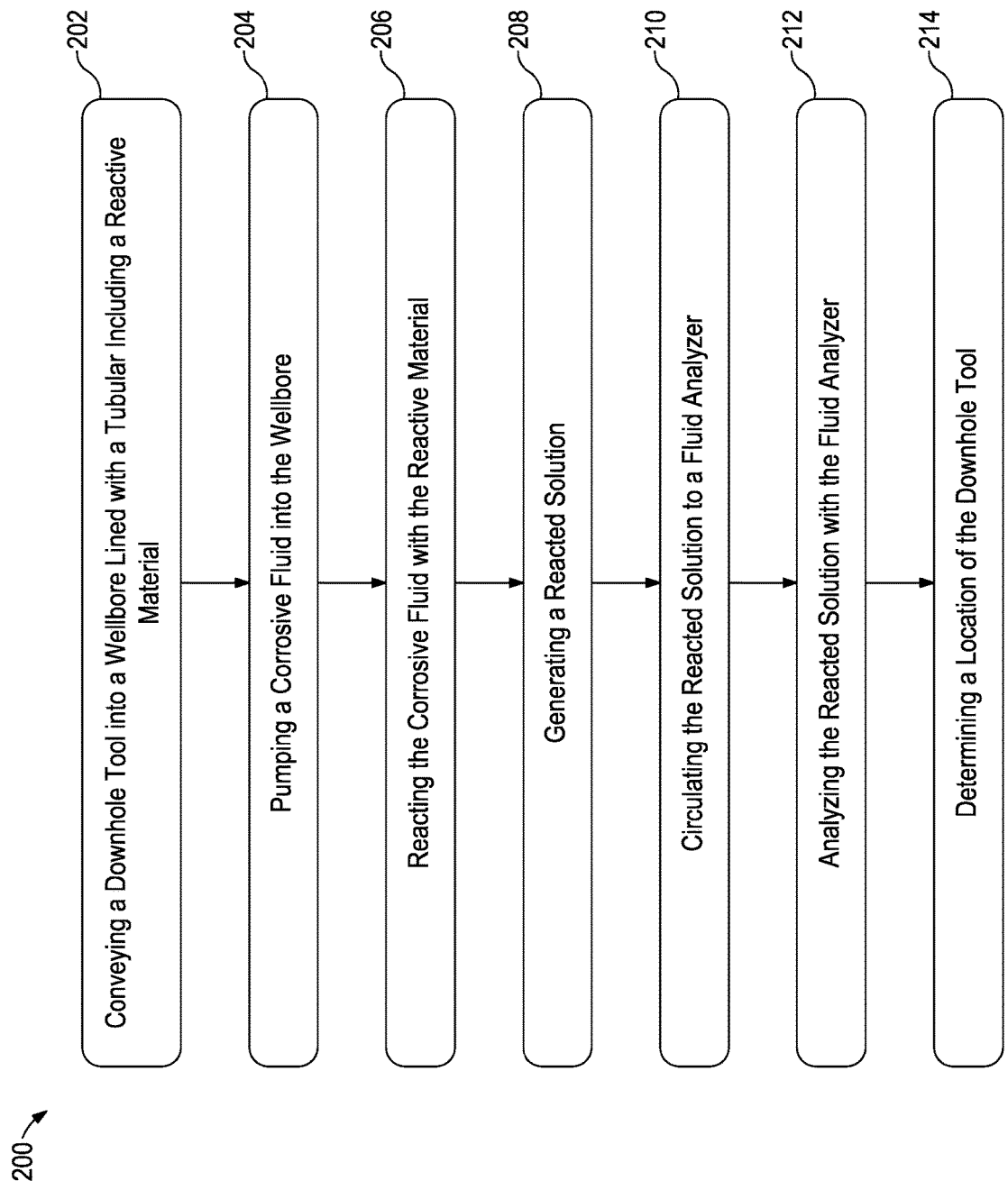
FIG. 2 is a schematic flowchart of an example method of entering a lateral wellbore of a multilateral wellbore, according to one or more embodiments.

FIG. 2 is a schematic flowchart of an example method 200 of entering a lateral wellbore of a multilateral wellbore, according to one or more embodiments. The method 200 may include conveying a downhole tool from a service rig and into a wellbore penetrating a subterranean formation, as at 202. The wellbore may include a primary wellbore and a first lateral wellbore extending from the primary wellbore. In some embodiments, the wellbore may include a plurality of lateral wellbores. The primary wellbore may include a casing wherein at least a portion of an inner surface of the casing is coated with a first reactive material. The first lateral wellbore may include a liner wherein in at least a portion of an inner surface of the liner is coated with a second reactive material that is different than the first reactive material. In embodiments including a plurality of lateral wellbores, each lateral wellbore may be lined with a corresponding liner having an inner surface coated with a corresponding reactive material, unique and different to that of the casing and other lateral wellbores. The method 200, may further include pumping a corrosive fluid to the downhole tool and then discharging the corrosive fluid from the downhole tool into the wellbore, as at 204.

The method 200 may continue by reacting the corrosive fluid with either the first or second reactive material, as at 206 and thereby generating a reacted solution that includes a reaction product, as at 208. The reacted solution including the reaction product may be circulated back to the service rig and into a fluid analyzer located on the service rig, as at 210. The method 200, progresses by analyzing the reacted solution with the fluid analyzer and thereby identifying the reaction product, as at 212. By identifying the reaction product, the location of the downhole tool may be determined, as at 214. Depending upon the results of the fluid analyzer, the method 200 may continue by re-positioning the downhole tool until the intended wellbore is entered.

Embodiments disclosed herein include:

A. A well system, comprising, a service rig positioned above a wellbore penetrating a subterranean formation, the wellbore including a primary wellbore and a lateral wellbore extending from the primary wellbore. The primary wellbore including a string of casing lining at least a portion of the primary wellbore and having an inner surface coated with a first reactive material and a liner lining at least a portion of the lateral wellbore and having an inner surface coated with a second reactive material different from the first reactive material. The well system further including a downhole tool conveyable into the wellbore from the service rig, the downhole tool being operable to discharge a corrosive fluid reactable with the first or second reactive material and generate a reacted solution that includes a reaction product indicative of the first or second reactive material. The well system also including a fluid analyzer arranged at the service rig and operable to analyze the reacted solution and identify the reaction product entrained in the reacted solution, wherein identifying the reaction product with the fluid analyzer provides a positive indication of a location of the downhole tool within the wellbore.

B. A method, comprising, conveying a downhole tool from a service rig and into a wellbore penetrating a subterranean formation, the wellbore including a primary wellbore extending from the service rig and lined with casing having a portion of an inner surface of the casing coated with a first reactive material and a lateral wellbore extending from the primary wellbore and lined with a liner having a portion of an inner surface of the liner coated with a second reactive material different from the first reactive material. The method including pumping a corrosive fluid to the downhole tool and discharging the corrosive fluid into the wellbore from the downhole tool. The method continuing by reacting the corrosive fluid with one of the first and second reactive materials and thereby generating a reacted solution including a reaction product indicative of the one of the first and second reactive materials. The method including circulating the reacted solution and the reaction product to the service rig, analyzing the reacted solution at the service rig with a fluid analyzer and thereby identifying the reaction product, and determining a location of the downhole tool within the wellbore based on identification of the reaction product.

C. A method, comprising, conveying a downhole tool from a service rig and into a wellbore penetrating a subterranean formation, the wellbore including a primary wellbore extending from the service rig, a first lateral wellbore extending from the primary wellbore and lined with a first liner having a portion of an inner surface of the first liner coated with a first reactive material; and a second lateral wellbore extending from the primary wellbore and lined with a second liner having a portion of an inner surface of the second liner coated with a second reactive material different from the first reactive material. The method including pumping a corrosive fluid to the downhole tool and discharging the corrosive fluid into the wellbore from the downhole tool. The method further including reacting the corrosive fluid with one of the first and second reactive materials and thereby generating a reacted solution including a reaction product indicative of the one of the first and second reactive materials. The method including circulating the reacted solution and the reaction product to the service rig. The method including analyzing the reacted solution at the service rig with a fluid analyzer and thereby identifying the reaction product and determining a location of the downhole tool within the first or second lateral wellbores based on identification of the reaction product.

Each of embodiments A, B, and C may have one or more of the following additional elements in any combination: Element 1: wherein the lateral wellbore forms part of a plurality of lateral wellbores extending from the primary wellbore, and wherein each lateral wellbore is lined with a corresponding liner having an inner surface of the corresponding liner coated with a corresponding reactive material, and each corresponding reactive material is unique. Element 2: wherein the downhole tool includes a steering tool operable to guide the downhole tool within the wellbore and is further operable to execute a stimulation treatment specific to each lateral wellbore comprising the plurality of lateral wellbores. Element 3: wherein the lateral wellbore comprises a first lateral wellbore and the liner comprises a first liner, the well system further comprising, a second lateral wellbore extending from the primary wellbore, and a second liner lining at least a portion of the second lateral wellbore and having an inner surface of the second liner coated with a third reactive material different from the first and second reactive materials, wherein the corrosive fluid is reactable with the third reactive material to generate the reacted solution including a reaction product indicative of the third reactive material, and wherein identifying the reaction product as indicative of the third reactive material with the fluid analyzer provides the positive indication that the downhole tool is located within the second lateral wellbore. Element 4: wherein the downhole tool includes a steering tool operable to guide the downhole tool within the wellbore. Element 5: wherein the fluid analyzer is operable to perform an analysis selected from the group consisting of mass spectrometry, x-ray fluorescence "XRF" spectroscopy, atomic absorption spectroscopy, fourier transform infrared spectroscopy (FTIR) ultraviolet-visible spectroscopy (UV-Vis), any combination thereof. Element 6: wherein the first and second reactive materials are selected from the group consisting of carbonate ($CaCO_3$), zinc (Zn), aluminum (Al), manganese (Mn), nickel (Ni), copper (Cu), and barium (Ba), and any combination thereof. Element 7: wherein the first and second reactive materials are chemically compatible with existing formation fluids originating in the subterranean formation, thereby not deteriorating in the presence of the formation fluids. Element 8: wherein the first and second reactive materials are chemically compatible with existing formation fluids originating in the subterranean formation, thereby not deteriorating in the presence of the formation fluids. Element 9: wherein the corrosive fluid comprises a chemical solution selected from the group consisting of hydrochloric acid (HCl), sulfuric acid ($H_2SO4$), nitric acid ($HNO_3$), acetic acid ($CH_3COOH$), phosphoric acid ($H_3PO_4$), formic acid (HCOOH), citric acid ($C_6H_8O_7$), and any combination thereof. Element 10: wherein selection of the reactive material includes consideration of characteristics selected from the drilling fluid used, the completion fluid used, the formation fluid used, the lithology of the formation, and any combination thereof. Element 11: wherein conveying the downhole tool into the wellbore comprises conveying the downhole tool into the wellbore via coiled tubing extending from the service rig. Element 12: wherein pumping the corrosive fluid to the downhole tool comprises pumping at least five barrels of the corrosive fluid to the downhole tool. Element 13: wherein the reacted solution comprises a first reacted solution, and the reaction product comprises a first reaction product indicative of the first reactive material, the method further comprising, retracting the downhole tool in an uphole direction, conveying the downhole tool in a downhole direction and changing a trajectory of the downhole tool to enter the first lateral wellbore, pumping the corrosive fluid to the downhole tool and discharging the corrosive fluid into first lateral wellbore, reacting the corrosive fluid with the second reactive material and thereby generating a second reacted solution including a second reaction product indicative of the second reactive material, circulating the second reacted solution and the second reaction product to the service rig, analyzing the second reacted solution at the service rig with the fluid analyzer and thereby identifying the second reaction product as indicative of the second reactive material, and determining that the downhole tool is within the first lateral wellbore based on identification of the second reaction product. Element 13: wherein the first and second reactive materials are selected from the group consisting of carbonate ($CaCO_3$), zinc (Zn), aluminum (Al), manganese (Mn), nickel (Ni), copper (Cu), and barium (Ba), and any combination thereof. Element 14: wherein conveying the downhole tool into the wellbore is preceded by coating the inner surface of the liner with the second reactive material at or near a kickoff point from the primary wellbore.

Element 15: wherein the reacted solution comprises a first reacted solution, and the reaction product comprises a first reaction product indicative of the first reactive material, the method further comprising, retracting the downhole tool in an uphole direction, conveying the downhole tool in a downhole direction and changing a trajectory of the downhole tool to enter the second lateral wellbore, pumping the corrosive fluid to the downhole tool and discharging the corrosive fluid into second lateral wellbore, reacting the corrosive fluid with the second reactive material and thereby generating a second reacted solution including a second reaction product indicative of the second reactive material, circulating the second reacted solution and the second reaction product to the service rig, analyzing the second reacted solution at the service rig with the fluid analyzer and thereby identifying the second reaction product as indicative of the second reactive material, and determining that the downhole tool is within the second lateral wellbore based on identification of the second reaction product. Element 16: wherein the first and second reactive materials are selected from the group consisting of carbonate ($CaCO_3$), zinc (Zn), aluminum (Al), manganese (Mn), nickel (Ni), copper (Cu), and barium (Ba), and any combination thereof. Element 17: wherein conveying the downhole tool into the wellbore comprises conveying the downhole tool into the wellbore via coiled tubing extending from the service rig.

By way of non-limiting example, an exemplary combination applicable to A, B and C includes: Element 1 with Element 2.

The terminology used herein is for the purpose of describing particular embodiments only and is not intended to be limiting of the invention. As used herein, for example, the singular forms "a," "an," and "the" are intended to include the plural forms as well, unless the context clearly indicates otherwise. It will be further understood that the terms "contains", "containing", "includes", "including," "comprises", and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Terms of orientation used herein are merely for purposes of convention and referencing and are not to be construed as limiting. However, it is recognized these terms could be used with reference to an operator or user. Accordingly, no limitations are implied or to be inferred. In addition, the use of ordinal numbers (e.g., first, second, third, etc.) is for distinction and not counting. For example, the use of "third" does not imply there must be a corresponding "first" or "second." Also, if used herein, the terms "coupled" or "coupled to" or "connected" or "connected to" or "attached" or "attached to" may indicate establishing either a direct or indirect connection, and is not limited to either unless expressly referenced as such.

While the disclosure has described several exemplary embodiments, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

The invention claimed is:

1. A well system, comprising:
    a service rig positioned above a wellbore penetrating a subterranean formation, the wellbore including a primary wellbore and a lateral wellbore extending from the primary wellbore;
    a string of casing lining at least a portion of the primary wellbore and having an inner surface coated with a first reactive material;
    a liner lining at least a portion of the lateral wellbore and having an inner surface coated with a second reactive material different from the first reactive material;
    a downhole tool conveyable into the wellbore from the service rig, the downhole tool being operable to discharge a corrosive fluid reactable with the first or second reactive material and generate a reacted solution that includes a reaction product indicative of the first or second reactive material; and
    a fluid analyzer arranged at the service rig and operable to analyze the reacted solution and identify the reaction product entrained in the reacted solution, wherein identifying the reaction product with the fluid analyzer provides a positive indication of a location of the downhole tool within the wellbore.

2. The well system of claim 1, wherein the lateral wellbore forms part of a plurality of lateral wellbores extending from the primary wellbore, and wherein each lateral wellbore is lined with a corresponding liner having an inner surface of the corresponding liner coated with a corresponding reactive material, and each corresponding reactive material is unique.

3. The well system of claim 2, wherein the downhole tool includes a steering tool operable to guide the downhole tool within the wellbore and is further operable to execute a stimulation treatment specific to each lateral wellbore comprising the plurality of lateral wellbores.

4. The well system of claim 1, wherein the lateral wellbore comprises a first lateral wellbore and the liner comprises a first liner, the well system further comprising:
    a second lateral wellbore extending from the primary wellbore; and
    a second liner lining at least a portion of the second lateral wellbore and having an inner surface of the second liner coated with a third reactive material different from the first and second reactive materials,
    wherein the corrosive fluid is reactable with the third reactive material to generate the reacted solution including a reaction product indicative of the third reactive material, and
    wherein identifying the reaction product as indicative of the third reactive material with the fluid analyzer provides the positive indication that the downhole tool is located within the second lateral wellbore.

5. The well system of claim 1, wherein the downhole tool includes a steering tool operable to guide the downhole tool within the wellbore.

6. The well system of claim 1, wherein the fluid analyzer is operable to perform an analysis selected from the group consisting of mass spectrometry, x-ray fluorescence "XRF" spectroscopy, atomic absorption spectroscopy, fourier transform infrared spectroscopy (FTIR) ultraviolet-visible spectroscopy (UV-Vis), any combination thereof.

7. The well system of claim 1, wherein the first and second reactive materials are selected from the group consisting of carbonate ($CaCO_3$), zinc (Zn), aluminum (Al), manganese (Mn), nickel (Ni), copper (Cu), and barium (Ba), and any combination thereof.

8. The well system of claim 1, wherein the first and second reactive materials are chemically compatible with existing formation fluids originating in the subterranean formation, thereby not deteriorating in the presence of the formation fluids.

9. The well system of claim 1, wherein the corrosive fluid comprises a chemical solution selected from the group consisting of hydrochloric acid (HCl), sulfuric acid ($H_2SO4$), nitric acid ($HNO_3$), acetic acid ($CH_3COOH$), phosphoric acid ($H_3PO_4$), formic acid (HCOOH), citric acid ($C_6H_8O_7$), and any combination thereof.

10. The well system of claim 1, wherein selection of the reactive material includes consideration of characteristics selected from the drilling fluid used, the completion fluid used, the formation fluid used, the lithology of the formation, and any combination thereof.

11. A method, comprising:
    conveying a downhole tool from a service rig and into a wellbore penetrating a subterranean formation, the wellbore including:
        a primary wellbore extending from the service rig and lined with casing having a portion of an inner surface of the casing coated with a first reactive material; and
        a lateral wellbore extending from the primary wellbore and lined with a liner having a portion of an inner surface of the liner coated with a second reactive material different from the first reactive material;

pumping a corrosive fluid to the downhole tool and discharging the corrosive fluid into the wellbore from the downhole tool;

reacting the corrosive fluid with one of the first and second reactive materials and thereby generating a reacted solution including a reaction product indicative of the one of the first and second reactive materials;

circulating the reacted solution and the reaction product to the service rig;

analyzing the reacted solution at the service rig with a fluid analyzer and thereby identifying the reaction product; and determining a location of the downhole tool within the wellbore based on identification of the reaction product.

12. The method of claim 11, wherein conveying the downhole tool into the wellbore comprises conveying the downhole tool into the wellbore via coiled tubing extending from the service rig.

13. The method of claim 11, wherein pumping the corrosive fluid to the downhole tool comprises pumping at least five barrels of the corrosive fluid to the downhole tool.

14. The method of claim 11, wherein the reacted solution comprises a first reacted solution, and the reaction product comprises a first reaction product indicative of the first reactive material, the method further comprising:

retracting the downhole tool in an uphole direction;

conveying the downhole tool in a downhole direction and changing a trajectory of the downhole tool to enter the first lateral wellbore;

pumping the corrosive fluid to the downhole tool and discharging the corrosive fluid into first lateral wellbore;

reacting the corrosive fluid with the second reactive material and thereby generating a second reacted solution including a second reaction product indicative of the second reactive material;

circulating the second reacted solution and the second reaction product to the service rig;

analyzing the second reacted solution at the service rig with the fluid analyzer and thereby identifying the second reaction product as indicative of the second reactive material; and determining that the downhole tool is within the first lateral wellbore based on identification of the second reaction product.

15. The method of claim 11, wherein the first and second reactive materials are selected from the group consisting of carbonate ($CaCO_3$), zinc (Zn), aluminum (Al), manganese (Mn), nickel (Ni), copper (Cu), and barium (Ba), and any combination thereof.

16. The method of claim 11, wherein conveying the downhole tool into the wellbore is preceded by coating the inner surface of the liner with the second reactive material at or near a kickoff point from the primary wellbore.

17. A method, comprising:

conveying a downhole tool from a service rig and into a wellbore penetrating a subterranean formation, the wellbore including:

a primary wellbore extending from the service rig;

a first lateral wellbore extending from the primary wellbore and lined with a first liner having a portion of an inner surface of the first liner coated with a first reactive material; and a second lateral wellbore extending from the primary wellbore and lined with a second liner having a portion of an inner surface of the second liner coated with a second reactive material different from the first reactive material;

pumping a corrosive fluid to the downhole tool and discharging the corrosive fluid into the wellbore from the downhole tool;

reacting the corrosive fluid with one of the first and second reactive materials and thereby generating a reacted solution including a reaction product indicative of the one of the first and second reactive materials;

circulating the reacted solution and the reaction product to the service rig;

analyzing the reacted solution at the service rig with a fluid analyzer and thereby identifying the reaction product; and determining a location of the downhole tool within the first or second lateral wellbores based on identification of the reaction product.

18. The method of claim 17, wherein the reacted solution comprises a first reacted solution, and the reaction product comprises a first reaction product indicative of the first reactive material, the method further comprising:

retracting the downhole tool in an uphole direction;

conveying the downhole tool in a downhole direction and changing a trajectory of the downhole tool to enter the second lateral wellbore;

pumping the corrosive fluid to the downhole tool and discharging the corrosive fluid into second lateral wellbore;

reacting the corrosive fluid with the second reactive material and thereby generating a second reacted solution including a second reaction product indicative of the second reactive material;

circulating the second reacted solution and the second reaction product to the service rig;

analyzing the second reacted solution at the service rig with the fluid analyzer and thereby identifying the second reaction product as indicative of the second reactive material; and determining that the downhole tool is within the second lateral wellbore based on identification of the second reaction product.

19. The method of claim 17, wherein the first and second reactive materials are selected from the group consisting of carbonate ($CaCO_3$), zinc (Zn), aluminum (Al), manganese (Mn), nickel (Ni), and any combination thereof.

20. The method of claim 17, wherein conveying the downhole tool into the wellbore comprises conveying the downhole tool into the wellbore via coiled tubing extending from the service rig.

* * * * *